(12) United States Patent
Chae et al.

(10) Patent No.: US 12,408,867 B2
(45) Date of Patent: Sep. 9, 2025

(54) AUXILIARY ADHESIVE PATCH OF BODY ATTACHABLE UNIT FOR CONTINUOUS BLOOD GLUCOSE MONITORING DEVICE

(71) Applicant: I-SENS, INC., Seoul (KR)

(72) Inventors: Kyung Chul Chae, Seoul (KR); Hyun Ho Choi, Seoul (KR); Goang Yel Ryu, Seoul (KR); Ji Hoon Wang, Seoul (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 797 days.

(21) Appl. No.: 17/631,492

(22) PCT Filed: Mar. 18, 2020

(86) PCT No.: PCT/KR2020/003707
§ 371 (c)(1),
(2) Date: Jan. 30, 2022

(87) PCT Pub. No.: WO2021/025259
PCT Pub. Date: Feb. 11, 2021

(65) Prior Publication Data
US 2022/0273239 A1    Sep. 1, 2022

(30) Foreign Application Priority Data

Aug. 7, 2019   (KR) .......................... 10-2019-0095971

(51) Int. Cl.
*A61B 5/00*     (2006.01)
*A61B 5/145*    (2006.01)

(52) U.S. Cl.
CPC ........ *A61B 5/6833* (2013.01); *A61B 5/14503* (2013.01); *A61B 5/14532* (2013.01); *A61B 5/68335* (2017.08); *A61B 5/6849* (2013.01)

(58) Field of Classification Search
CPC .............. A61B 5/6833; A61B 5/68335; A61B 5/14503; A61B 5/14532; A61B 5/1459;
(Continued)

(56) References Cited

U.S. PATENT DOCUMENTS

| 2016/0058380 | A1  | 3/2016 | Lee et al. |
| 2016/0213322 | A1* | 7/2016 | Goldberg ............ A61F 13/0259 |
| 2021/0236028 | A1* | 8/2021 | McCanless ........ A61B 5/14503 |

FOREIGN PATENT DOCUMENTS

| EP | 2 868 341    | 8/2018 |
| JP | 2014-147837  | 8/2014 |

(Continued)

OTHER PUBLICATIONS

Examination Report No. 1 dated Mar. 24, 2023 for Australian Patent Application No. 2020326036.
(Continued)

*Primary Examiner* — Devin B Henson
(74) *Attorney, Agent, or Firm* — WOMBLE BOND DICKINSON (US) LLP

(57) ABSTRACT

The present disclosure relates to an auxiliary adhesive patch of a body attachment unit for a continuous blood glucose monitoring device. The present invention provides an auxiliary adhesive patch of a body attachment unit for a continuous blood glucose monitoring device, which: includes a separate over-patch surrounding an adhesive tape of a body attachment unit and attached to a skin, so that the size of the adhesive tape of the body attachment unit can be kept to be minimum and, in this state, the body attachment unit can be additionally attached and fixed to the skin so as to strengthen the adhesive force thereof; and has a plurality of release sheets attached to an adhesive surface of the over-patch, wherein each of the release sheets is separately formed and has a protection area formed to include an adhesive area and a part of a pressurization area of the over-patch, so that, in (Continued)

the process of detaching the release sheets, the position of the over-patch can be stably held and the over-patch can thus be attached conveniently and rapidly.

7 Claims, 9 Drawing Sheets

(58) Field of Classification Search
CPC . A61B 5/1473; A61B 5/14865; A61B 5/6849; A61B 5/685
USPC .............................................. 428/40.1, 41.8
See application file for complete search history.

(56) References Cited

FOREIGN PATENT DOCUMENTS

| | | |
|---|---|---|
| JP | 2018-102576 | 7/2018 |
| KR | 10-2011-0106234 | 9/2011 |
| KR | 20-2016-0000830 | 3/2016 |
| KR | 10-2017-0027646 | 3/2017 |
| KR | 10-2018-0121487 | 11/2018 |
| KR | 10-2018-0121587 | 11/2018 |
| KR | 10-2018-0132552 | 12/2018 |

OTHER PUBLICATIONS

Examination Report No. 1 dated Oct. 3, 2023 for New Zealand Patent Application No. 784523.
Office Action for Japanese Patent Application No. 2022-503993 issued on Dec. 13, 2022 and its English translation from Global Dossier.
International Preliminary Report on Patentability (Chapter I) for PCT/KR2020/003707 issued on Feb. 8, 2022 and its English translation from WIPO (now published as WO 2021/025259).
Extended European Search Report dated Aug. 2, 2023 for European Patent Application No. 20850149.4.
International Search Report for PCT/KR2020/003707 mailed on Jul. 2, 2020 and its English translation from WIPO (now published as WO 2021/025259).
Written Opinion of the International Searching Authority for PCT/KR2020/003707 mailed on Jul. 2, 2020 and its English translation by Google Translate (now published as WO 2021/025259).
Office Action dated Oct. 29, 2020 for Korean Patent Application No. 10-2019-0095971 and its English translation from Global Dossier.
Office Action dated Jun. 25, 2021 for Korean Patent Application No. 10-2019-0095971 and its English translation from Global Dossier.

* cited by examiner

[Fig. 1]
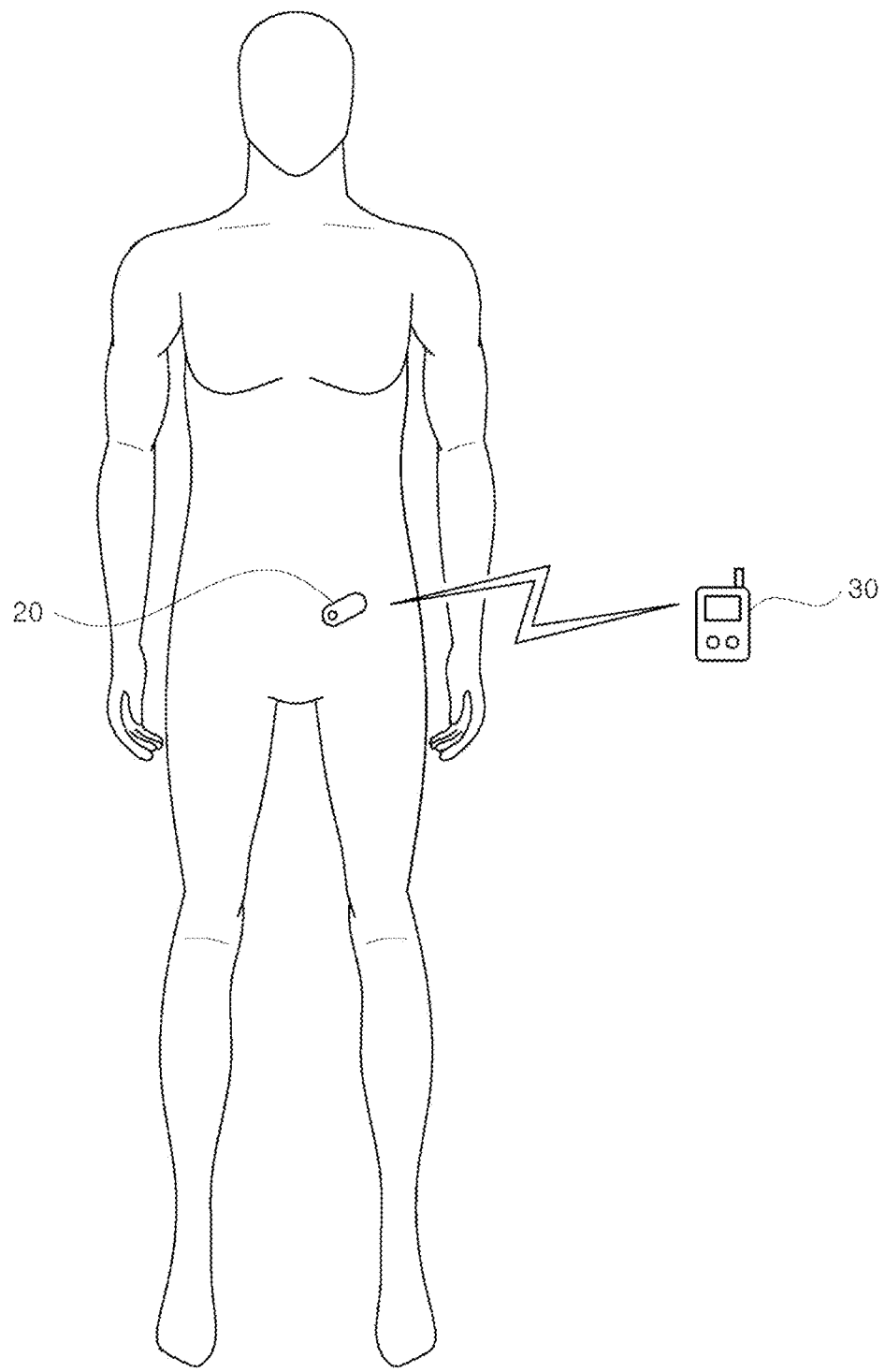

[Fig. 2]
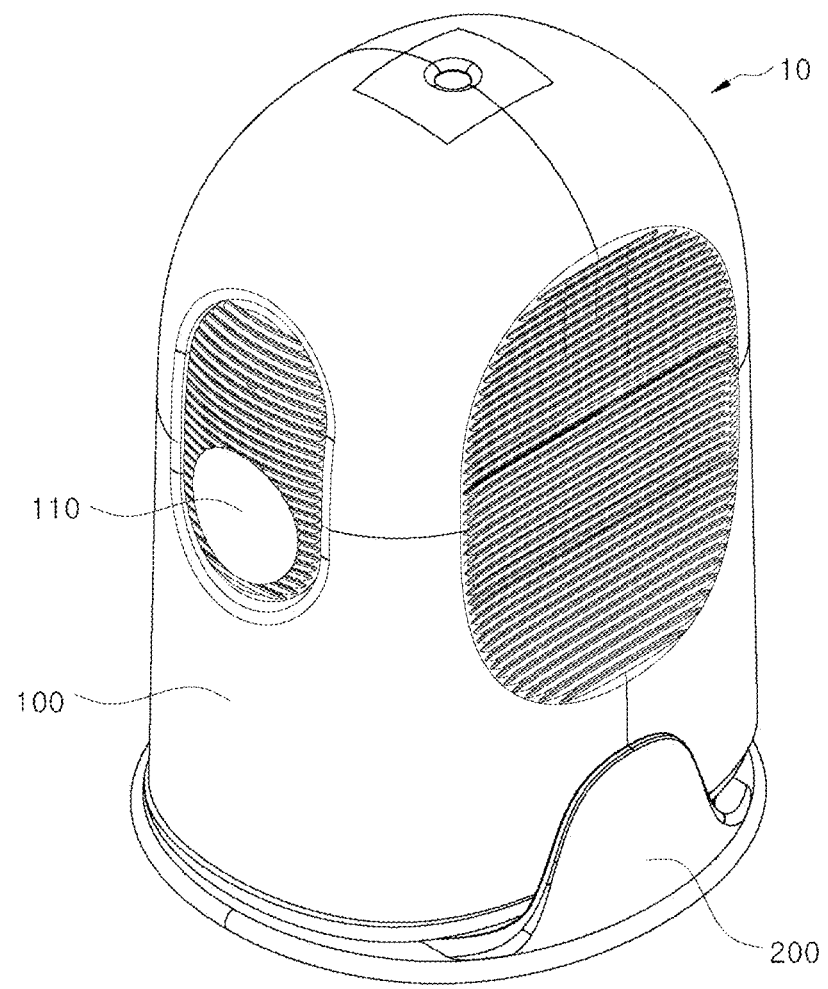

[Fig. 3]
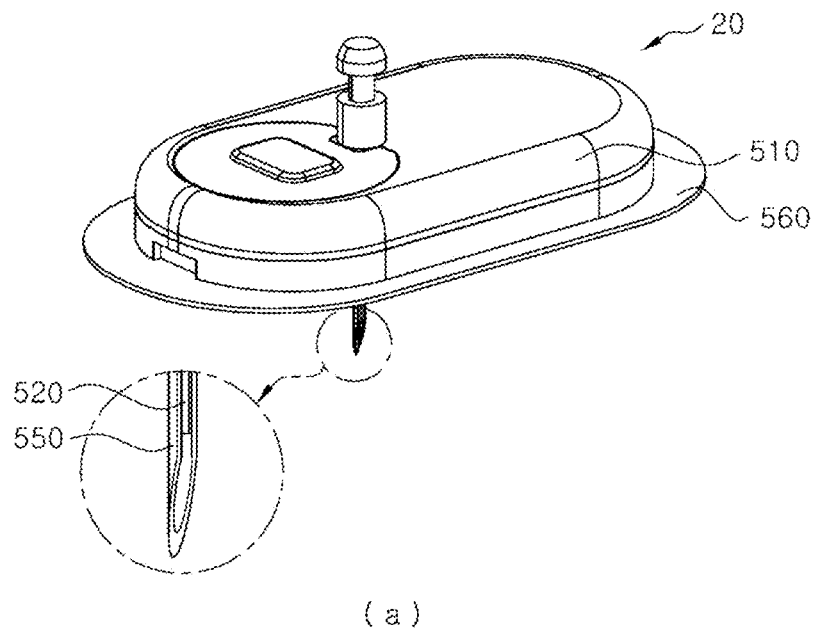
(a)
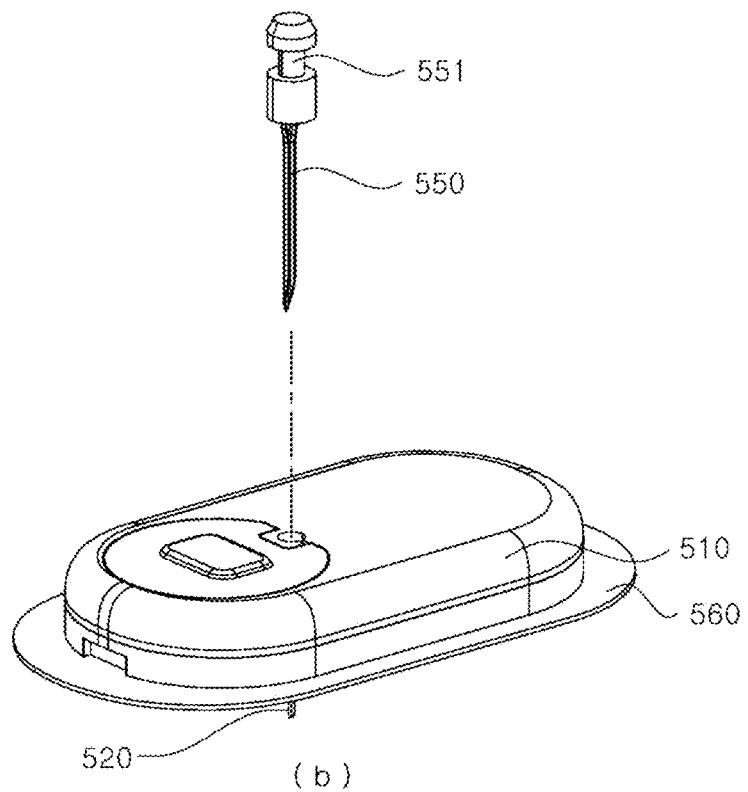
(b)

[Fig. 4]
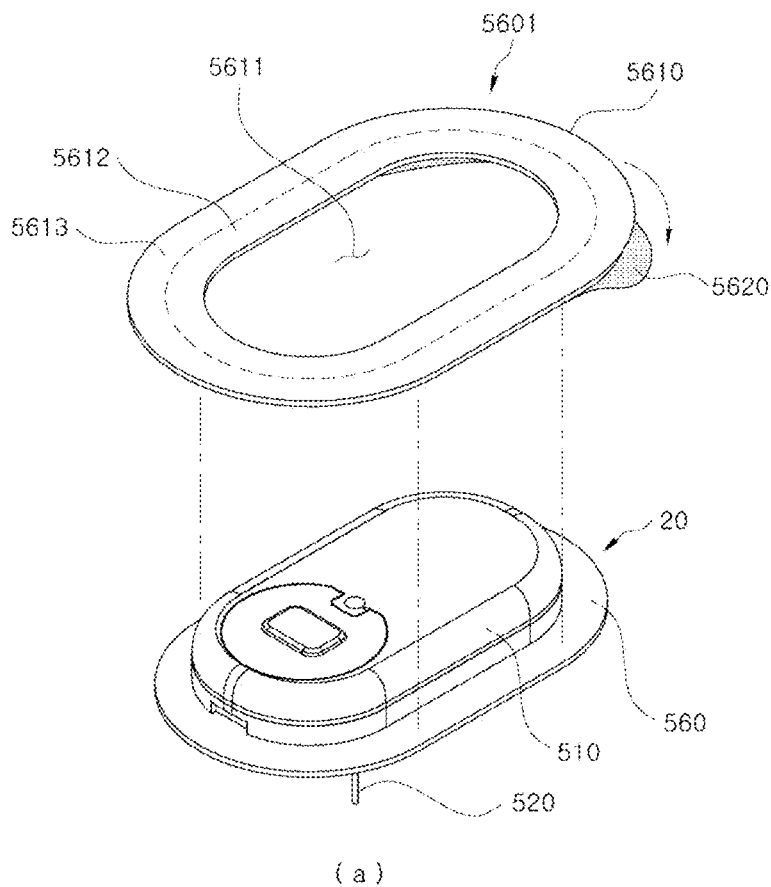
(a)
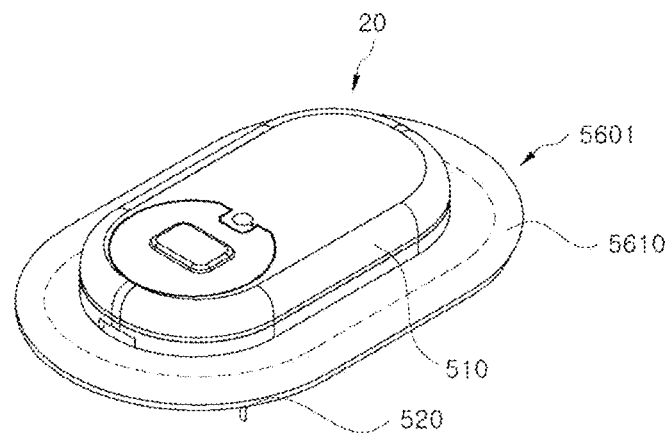
(b)

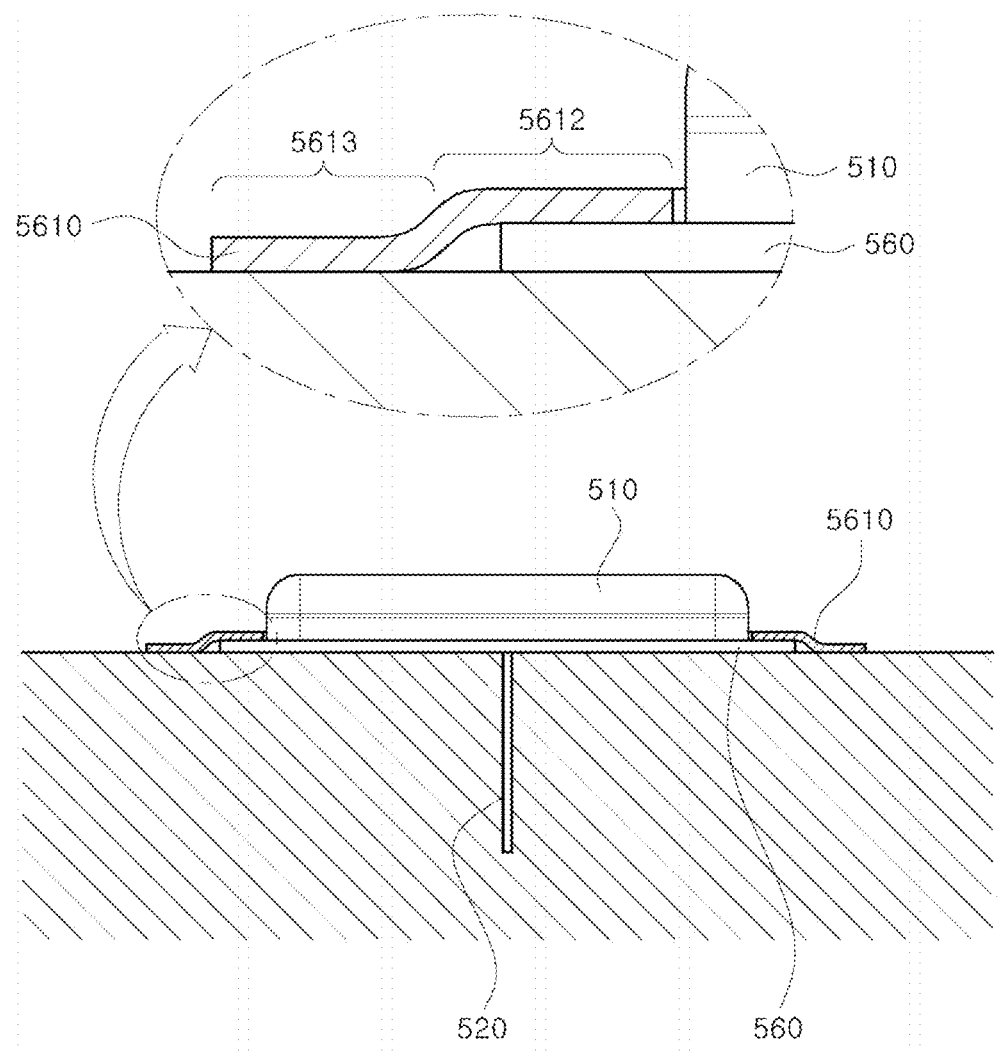
[Fig. 5]

[Fig. 6]
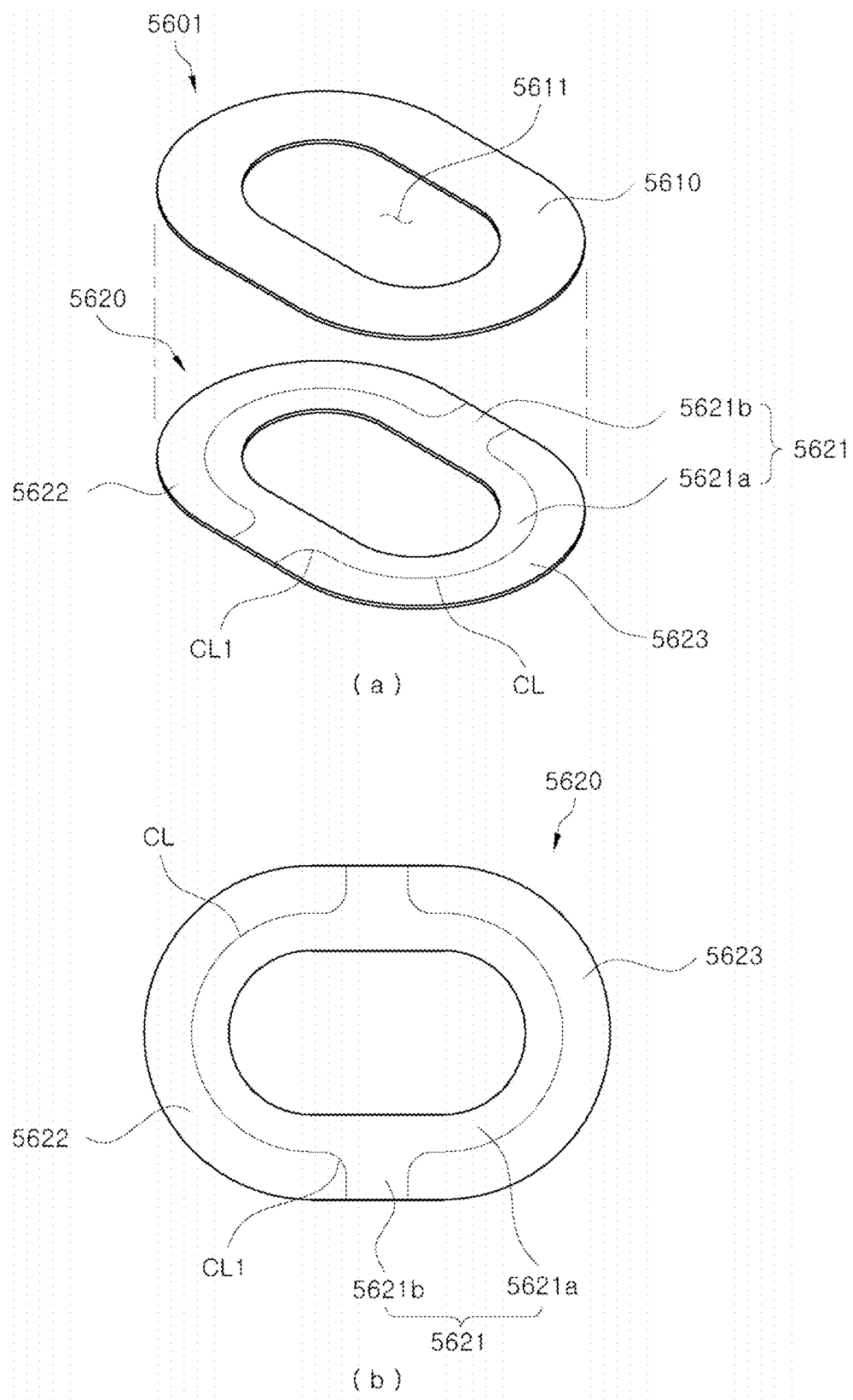

[Fig. 7]
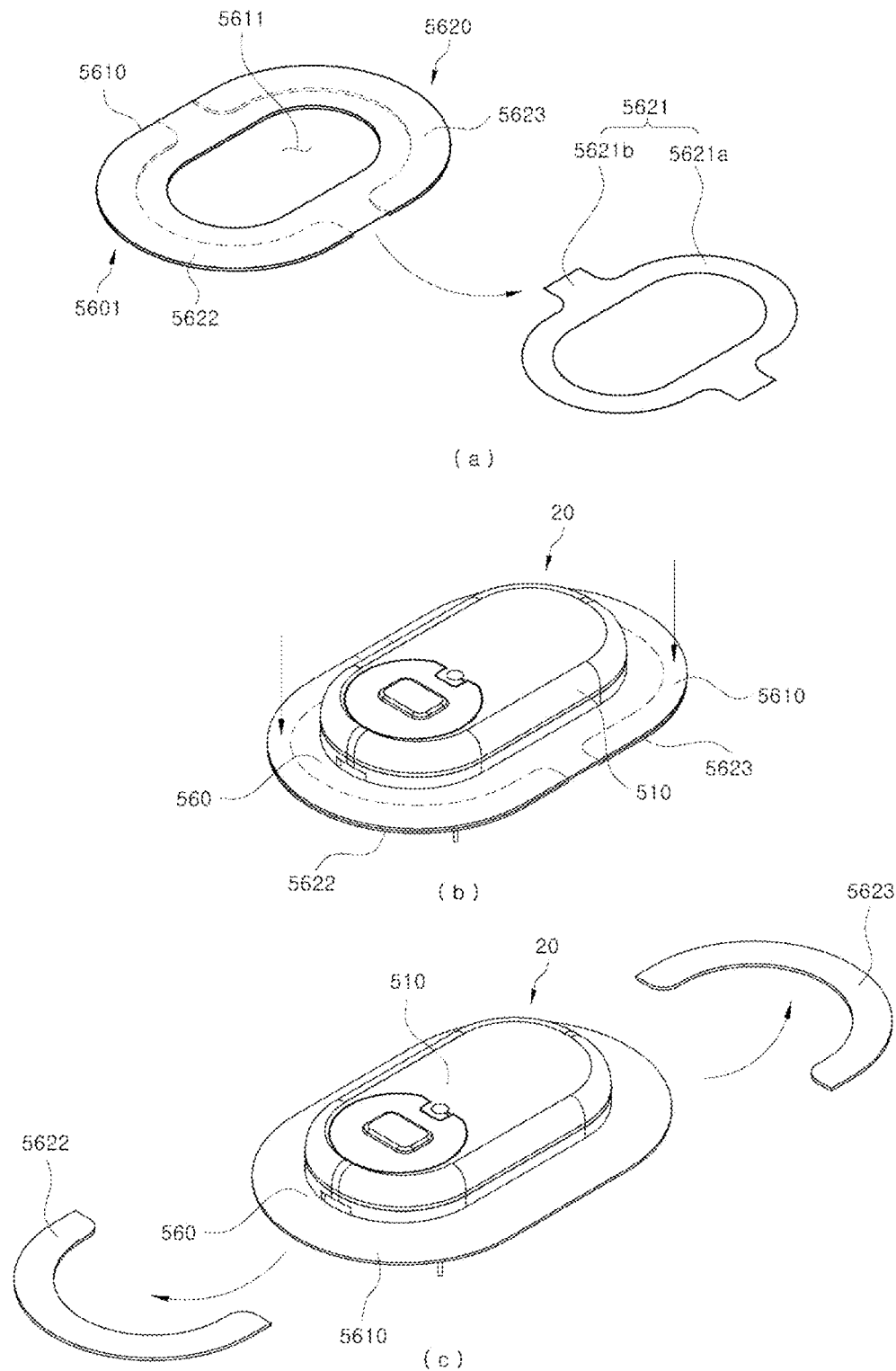

[Fig. 8]
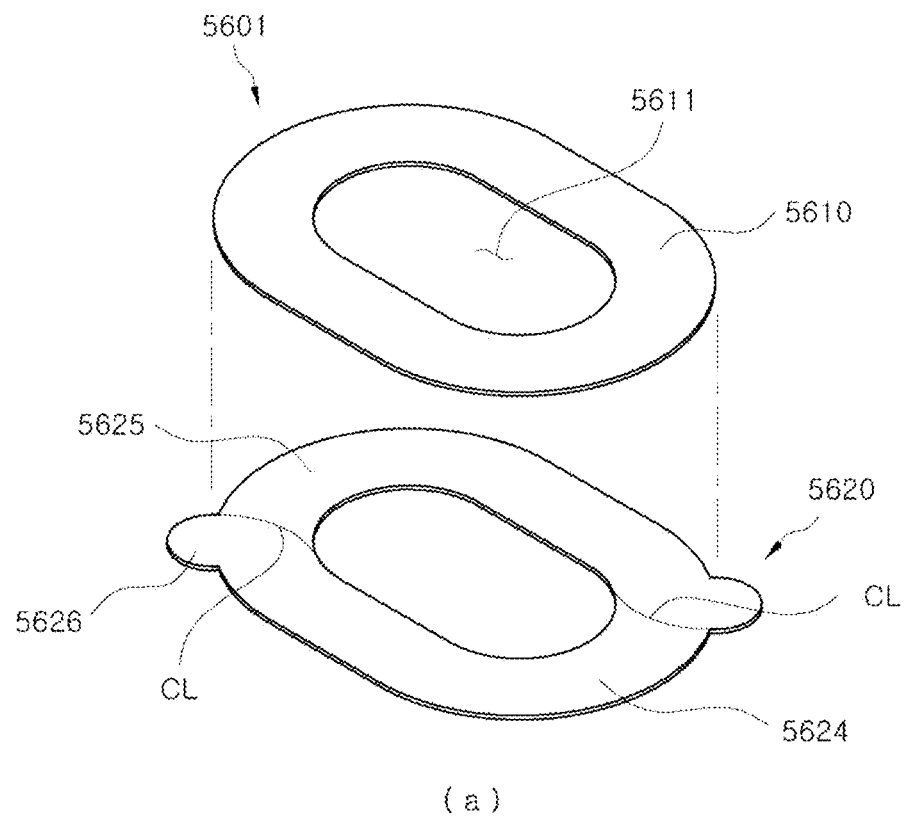
(a)
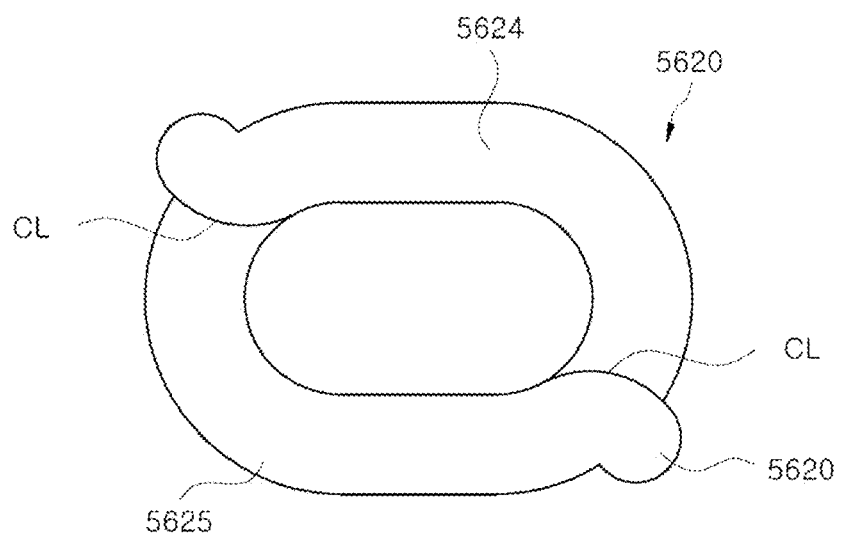
(b)

[Fig. 9]
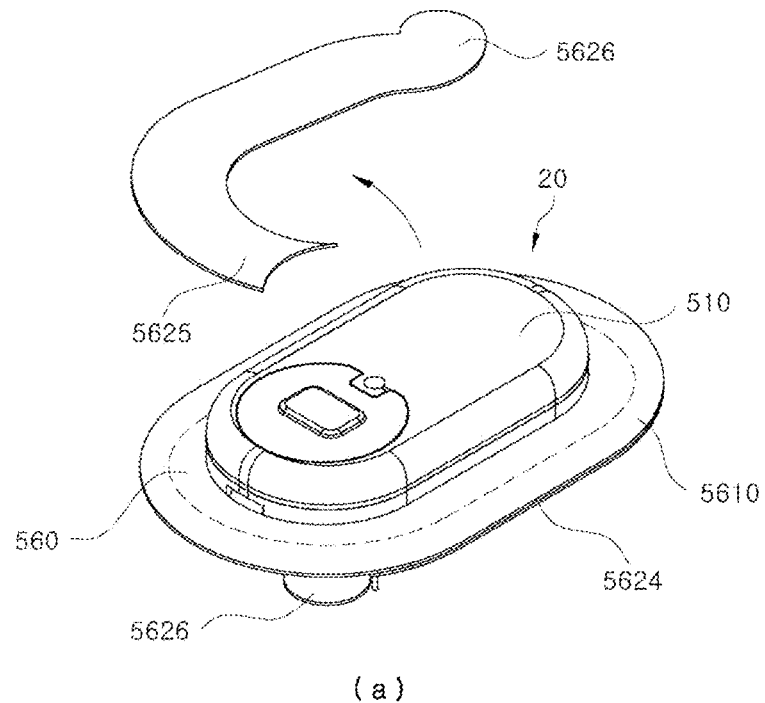
(a)
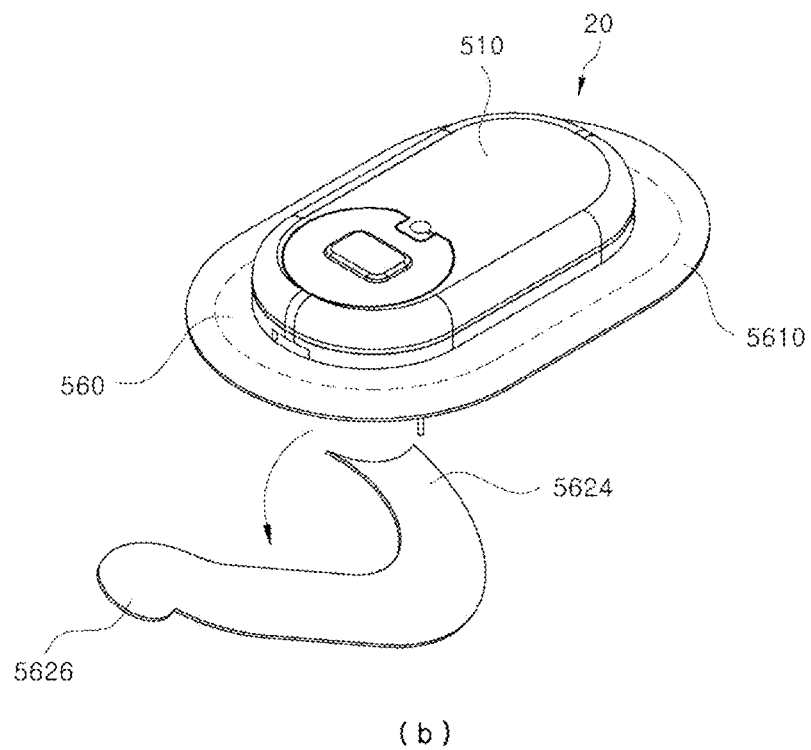
(b)

AUXILIARY ADHESIVE PATCH OF BODY ATTACHABLE UNIT FOR CONTINUOUS BLOOD GLUCOSE MONITORING DEVICE

CROSS-REFERENCE TO RELATED APPLICATIONS

The present application is the U.S. National Phase of PCT Application No. PCT/KR2020/003707 filed on Mar. 18, 2020, which claims the priority to Korean Patent Application No. 10-2019-0095971 filed on Aug. 7, 2019, the entire contents of which are incorporated herein by reference.

TECHNICAL FIELD

The present disclosure generally relates to an auxiliary adhesive patch of a body attachable unit for a continuous blood glucose monitoring device. In more detail, the present disclosure relates to an auxiliary adhesive patch of a body attachable unit for a continuous blood glucose monitoring device in which, by having an over patch covering an adhesive tape of a body attachable unit and attached to skin, the size of the adhesive tape of the body attachable unit is maintained to be minimized and in that state the body attachable unit can be additionally fixedly adhered to the skin, thereby reinforcing adhesive force, a release paper attached to an adhesive side of the over patch is formed to be separable into multiple pieces, each protection area of the release paper includes a part of an adhesive area and a part of a pressurizing area of the over patch, thereby stably fixing the position of the over patch during a release paper separation process, and therefore the adhesive operation of the over patch can be performed conveniently and rapidly.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. Cygnus Corporation, Redwoo City, Calif., U.S.A., has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, and an adhesive tape is attached to an outer housing of the sensor module so that the sensor module can be attached to the human body. If the sensor module is attached to the human body skin through the applicator according to this structure, a state that the sensor module is attached to the human body skin is maintained by the adhesive tape, and, the blood glucose is continuously measured in this state.

An adhesive tape needs to be formed to be larger than the sensor module and attached to the skin for reinforcing adhesive force to the skin, and if the size of the adhesive tape is made larger, the size of the applicator should also become increased, and this can cause inconvenience in use and the increase of the manufacturing cost, and there may be problems of having the limitations to shape and design perspectives. If the adhesive tape is formed only on the bottom surface of the housing of the sensor module to avoid those problems, adhesive force may be weakened, thereby causing problems that the sensor module can be separated from the body skin for long term use.

SUMMARY

Technical Problem

The present disclosure is invented to solve problems in conventional technique, and the purpose of the present disclosure is for providing an auxiliary adhesive patch of a body attachable unit for a continuous blood glucose monitoring device including an over patch covering an adhesive tape of a body attachable unit and attached to skin, thereby maintaining the size of the adhesive tape of the body attachable unit to be minimized, in this state, being capable of additionally adhesively fixing the body attachable unit to the skin, thereby reinforcing adhesive force, and therefore not needing to enlarge the size of an application, thereby reducing manufacturing cost, improving use convenience and being possible to be applied to various shape and design.

Another purpose of the present disclosure is for providing an auxiliary adhesive patch of a body attachable unit for a continuous blood glucose monitoring device in which a release paper attached to an adhesive side of a over patch is formed to be separable into multiple pieces, each protection area of the release paper includes a part of an adhesive area and a part of a pressurizing area of the over patch, thereby stably fixing the position of the over patch during a release paper separation process, and therefore the adhesive operation of the over patch can be performed conveniently and rapidly.

Solution to Problem

According to an embodiment of the present disclosure, an auxiliary adhesive patch of a body attachable unit which is capable of adhesively fixing to skin the body attachable unit for continuous blood glucose measurement comprising a housing configured to receive a sensor unit configured to be insertable into a body for the continuous blood glucose measurement inside the housing, and an adhesive tape arranged to a bottom surface of the housing and outwardly protruding along an outer portion circumference of the housing, the auxiliary adhesive patch may comprise: an over patch, wherein an adhesive side is formed at one side of the over patch, a penetrating hole which the housing is capable of penetrating is formed at a center area of the over parch, and the adhesive side of the over patch has a pressurizing area formed along a outer circumference of the penetrating hole and configured to pressurize an area of the adhesive tape outwardly protruding from an outer portion circumference of the housing and be adhered with the adhesive tape, and an adhesive area formed along an outer portion circumference of the pressuring area and configured to be adhered to the skin; and a release paper attached to the adhesive side of the over patch in a form of being separable and removable by a user to protect the adhesive side of the over patch, wherein the release paper is cut into multiple pieces separably formed, wherein each of the multiple pieces of the release paper is independently removable from the over patch.

In the present embodiment, at least one of the multiple pieces of the release paper maybe attached to the adhesive side of the over patch to be formed to protect both a part of the pressurizing area and a part of the adhesive area of the over patch.

Further, the release paper may be separably formed to be cut into a position fixing release paper, a first adhesive release paper and a second adhesive release paper, and the position fixing release paper may comprise a pressurizing area protection portion protecting a whole area of the pressurizing area of the over patch, and an adhesive area protection portion protecting a part of the adhesive area in a structure of outwardly protruding at one side of the pressurizing area protection portion.

Additionally, the pressurizing area protection portion may be formed to be in a ring structure along the pressuring area of the over patch, and the adhesive area protection portion may be formed such that one side and another side of the adhesive area are symmetric to each other with respect to a center of the pressurizing area protection portion.

Further, the first adhesive release paper and the second adhesive release paper may be arranged at an outside of the pressurizing area protection portion of the position fixing release paper and are formed to protect a remaining part of the adhesive area of the over patch.

Additionally, the first adhesive release paper and the second adhesive release paper may be spaced apart from each other and symmetric to each other with respect to two of the adhesive area protection portion formed at the position fixing release paper.

Further, a connection portion of the adhesive area protection area with the pressurizing area protection portion may be formed to have a curved cut line, and the first adhesive release paper and the second adhesive release paper may be formed to be separably cuttable from the adhesive area protection portion along the curved cut line.

Additionally, the release paper may be formed to be separably cuttable into a first separation release paper and a second separation release paper, and the first separation release paper and the second separation release paper may be formed to protect a part of the pressurizing area and a part of the adhesive area, respectively, and may be formed to protect a whole area of the adhesive side of the over patch by dividing the whole area of the adhesive side of the over patch into two along a mutual cut line.

In addition, handle portions outwardly protruding toward an outside of the over patch may be formed at the first separation release paper and the second separation release paper, respectively.

Further, the handle portions of the first separation release paper and the second separation release paper may be formed to be opposed to each other at a portion adjacent to the mutual cut line.

Advantageous Effects of Invention

According to the present disclosure, there are technical effects of, by including an over patch covering an adhesive tape of a body attachable unit and attached to skin, maintaining the size of the adhesive tape of the body attachable unit to be minimized, in this state, by being capable of additionally adhesively fixing the body attachable unit to the skin, reinforcing adhesive force, and therefore by not needing to enlarge the size of an application, reducing manufacturing cost, improving use convenience and being possible to be applied to various shape and design.

Additionally, there are technical effects that a release paper attached to an adhesive side of an over patch is formed to be separable into multiple pieces, each protection area of the release paper includes a part of an adhesive area and a part of a pressurizing area of the over patch, thereby stably fixing the position of the over patch during a release paper separation process, and therefore the adhesive operation of the over patch can be performed conveniently and rapidly.

BRIEF DESCRIPTION OF THE DRAWINGS

FIG. 1 is a figure of schematically illustrating a basic system of a continuous blood glucose monitoring device according to an embodiment of the present disclosure.

FIG. 2 is a figure for schematically illustrating a structure of an applicator of a continuous blood glucose monitoring device according to an embodiment of the present disclosure.

FIG. 3 is a figure of schematically illustrating a configuration of a body attachable unit of a continuous blood glucose monitoring device according to an embodiment of the present disclosure.

FIG. 4 is a perspective view for schematically illustrating a configuration of an auxiliary adhesive patch of a body attachable unit according to an embodiment of the present disclosure.

FIG. 5 is a cross-sectional view for schematically illustrating an attachment status of an auxiliary adhesive patch of a body attachable unit according to an embodiment of the present disclosure.

FIG. 6 is a figure for schematically illustrating a configuration of an auxiliary adhesive patch according to an embodiment of the present disclosure.

FIG. 7 is a use status figure for schematically illustrating a use state of an auxiliary adhesive patch illustrated in FIG. 6.

FIG. 8 is a figure for schematically illustrating a configuration of an auxiliary adhesive patch according to another embodiment of the present disclosure.

FIG. 9 is a use status figure for schematically illustrating a use state of an auxiliary adhesive patch illustrated in FIG. 8.

DETAILED DESCRIPTION OF EMBODIMENTS

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

FIG. 1 is a figure of schematically illustrating a basic system of a continuous blood glucose monitoring device according to an embodiment of the present disclosure, FIG. 2 is a figure for schematically illustrating a structure of an applicator of a continuous blood glucose monitoring device according to an embodiment of the present disclosure, and FIG. 3 is a figure of schematically illustrating a configuration of a body attachable unit of a continuous blood glucose monitoring device according to an embodiment of the present disclosure.

A continuous blood glucose monitoring device according to an embodiment of the present disclosure is configured that a body attachable unit (20) including a sensor unit (520) inserted into the human body for continuous blood glucose measurement is configured to be attached to the human body through an applicator (10), the blood glucose can be continuously monitored by insertedly attaching the body attachable unit (20) to the human body by manipulating the applicator (20), and blood glucose information periodically measured by the body attachable unit (20) is transmitted to a terminal (30) to display it.

A continuous blood glucose monitoring apparatus may be manufactured as one single unit product by assembling a body attachable unit (20) into the inside of an applicator (10), and has a simpler structure which can be easily used by minimizing additional work of a user when using the continuous blood glucose monitoring apparatus.

The body attachable unit (20) may be configured to be attachable to a human body to periodically measure blood sugar level or glucose by extracting body fluid, and transmit the blood glucose measurement result to an external device such as an external terminal (30) and so on. A sensor unit (520) of which one end portion can be inserted into the human body and a wireless communication chip configured to wirelessly communicate with the external terminal (30) can be disposed inside the body attachable unit (20), and therefore, the body attachable unit (20) can be used without additional connection of a separate transmitter.

The applicator (10) is formed such that the body attachable unit (20) is fixedly coupled to inside of the applicator (10), and the applicator (10) is configured to outwardly discharge the body attachable unit (20) according to the manipulation of the user.

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, the sensor applicator assembly according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is supplied to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip (540), no connection with an extra transmitter is needed and therefore it can be used more conveniently.

In a conventional continuous blood glucose measurement apparatus, after removing a body attachable unit, which is separately packaged, precisely inserting it into an applicator, and then operating the applicator, the body attachable unit is attached to a skin, but the work precisely inserting the body attachable unit into the applicator is cumbersome as well as difficult and there is a problem in lowering the accuracy of blood glucose measurement because of contaminating the body attachable unit when young children or elderly adults perform this procedure.

In an embodiment of the present disclosure, at the manufacturing stage, it is manufactured and distributed in a state that the body attachable unit (20) is inserted in the applicator (10), and therefore the step that the user removes the body attachable unit (20) from the package and inserts it into the applicator (10) may be omitted, because the body attachable unit (20) can be attached to the skin by simply manipulating the applicator (10), the usability may be significantly improved, and specifically, the accuracy of blood glucose measurement may be improved by preventing the contamination of the body attachable unit (20).

A separate and additional protection cap (200) can be separably coupled to the applicator (10) in order to block external exposure in a state that the applicator (10) is inserted in the inside of the applicator (10), and it may be configured that the user can attach the body attachable unit (20) to the human body by manipulating the applicator (10) only after the protection cap (200) is separated.

In the embodiment of the present disclosure, an adhesive tape (560) is provided at a side of the body attachable unit (20) contacting the human body to be attached to the human body, to protect the adhesive tape (560), a release paper (not shown) is attached to a surface of the adhesive tape (560) contacting the human body, and the release paper of the adhesive tape (560) may be configured to be separated and removed from the adhesive tape (560) during the operation of separating the protection cap (200) from the applicator (10).

For example, the release paper of the adhesive tape (560) may be configured to adhere one side of the release paper to the protection cap (200), and therefore, if the user separates the protection cap (200) from the applicator (10), the release paper (560) may be separated and removed from the adhesive tape (560) together with the protection cap (200). Accordingly, if the user separates the protection cap (200), the release paper of the adhesive tape (560) is separated and removed, and therefore in this status the body attachable unit (20) can be attached to the human body by the operation of the applicator (10).

Additionally, in a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

Meanwhile, the body attachable unit (20) according to an embodiment of the present disclosure is configured to cause the sensor unit (520) and the wireless communication chip to initiate their operations through a separate switching means controlled by the user. Accordingly, after inserting and attaching the body attachable unit (20) to the human body by using the applicator (10), the user may initiate to operate the body attachable unit (20) through the switching means or other appropriate means included in the body attachable unit (20), and from the time of the initiation of the operation the sensor unit (520) and the wireless communication chip may be operated, the blood glucose of the human body may be measured, and the measurement result may be transmitted to the external terminal. In this embodiment, the switching means operated by the user may be implemented in various ways.

Additionally, in the body attachable unit (20), the sensor unit (520) is disposed in a housing (510), and one end portion of the sensor unit (520) outwardly protrudes from the housing (510) so that it can be inserted and attached to the human body. The sensor unit (520) may comprise a sensor probe unit to be inserted into the human body, and a sensor body unit disposed inside the housing (510), and the sensor probe and the sensor body unit are formed as one end portion and another end portion of the sensor unit (520), respectively, and in a bent shape.

In this embodiment, in order to smoothly perform the body insertion process of the sensor unit (520), an insertion guide needle (550) may be separatably coupled to the housing (510). The insertion guide needle (550) may surround one end portion of the sensor unit (520) and be configured to be inserted together with the sensor unit (520) into the human body so that one end portion of the sensor unit (520) can be stably inserted into the human body.

As shown in FIG. 3, the insertion guide needle (550) may be separatably coupled to the housing (510) in a direction penetrating the top and bottom of the housing (510) of the body attachable unit (20), the insertion guide needle (550) may be formed to have a structure covering the outside of the sensor unit (520), and a need head (551) is formed at the upper end portion of the needle unit (550). If the body attachable unit (20) is moved in the direction outwardly discharged by the applicator (10), the insertion guide needle (550) is inserted into the human body first before the sensor unit (520) is inserted into the human body and the insertion guide needle (550) may support the sensor unit (520) such that the sensor unit (520) can be stably inserted in the skin. The insertion guide needle (550) may be coupled with a needle extracting body (not shown) of the applicator (10) through the needle head (551), and after the body attachable unit (20) is inserted and attached to the human body by the operation of the applicator (10), the insertion guide needle (550) may be configured to be withdrew and removed from the human body by the needle extracting body of the applicator (10).

Meanwhile, an adhesive tape (560) is attached to the bottom surface of the housing (510) of the body attachable unit (20) so that the body attachable unit (20) can be attached to the human body skin, and the adhesive tape (560) is formed to outwardly protrude along the outmost edge of the housing (510). As described in the Background section, if the size of the adhesive tape (560) is made larger for reinforcing adhesive force, the size of the applicator (10) should become increased, and this can cause the increase of the manufacturing cost and use inconvenience, and make against shape and design perspectives.

Accordingly, the continuous blood glucose monitoring device according to an embodiment of the present disclosure maintains the size of the adhesive tape (560) to be minimized and, in this state, comprises an auxiliary adhesive patch (5601) configured to additionally adhesively fix the body attachable unit (20) to the skin.

Detailed configuration regarding the auxiliary adhesive patch (5601) according to an embodiment of the present disclosure will be described.

FIG. 4 is a perspective view for schematically illustrating a configuration of an auxiliary adhesive patch of a body attachable unit according to an embodiment of the present disclosure, and FIG. 5 is a cross-sectional view for schematically illustrating an attachment status of an auxiliary adhesive patch of a body attachable unit according to an embodiment of the present disclosure.

The auxiliary adhesive patch (5601) according to an embodiment of the present disclosure is configured to comprise an over patch (5610), and a release paper (5620) attached to an adhesive side of the over patch (5610).

The adhesive side is formed at one side of the over patch (5610), and a penetrating hole (5611) which the housing (510) can penetrate is formed at the center area of the over patch (5610). A pressurizing area (5612) formed along the outside circumference of the penetrating hole (5611) and configured to pressurize an area of the adhesive tape (560) outwardly protruded from an edge circumference of the housing (510) and be adhesive with the adhesive tape (560), and an adhesive area (5613) formed along the outside circumference of the pressurizing area (5612) and configured to be adhesive to the skin are formed at the adhesive side.

The release paper (5620) is attached to the adhesive side of the over patch (5610) in a form of being removably separable by the user to protect the adhesive side of the over patch (5610).

At that time, the release paper (5620) is cut in multiple pieces formed to be separable so that each can be independently separable and removable from the over patch (5610), and detailed descriptions regarding this will be described below with reference to FIGS. 6 to 9.

As illustrated in FIGS. 4 and 5, the over patch (5610) has the pressurizing area (5612) pressurizingly attached to the adhesive tape (560) area outwardly protruded from the edge circumference of the housing (510), and the adhesive area (5613) formed at the outside area of the pressurizing area (5612) and configured to be attachable to the human body skin, and therefore the over patch (5610) can additionally adhesively fix the body attachable unit (20) to the skin.

Accordingly, because in a state of being bonded with the adhesive tape (560) of the housing (510) bottom side through the pressurizing area (5612) of the over patch (5610) the adhesive extent which is attached to the skin is increased through the adhesive area (5613), and therefore the body attachable unit (20) is additionally adhesively fixed to the skin in the form of covering the outside of the body attachable unit (20).

After the user attaches the body attachable unit (20) to the human body through the applicator (10), such an over patch (5610) is used in a form of covering and bonding the outer circumference of the body attachable unit (20) attached to the human body.

Accordingly, the continuous blood glucose monitoring device according to an embodiment of the present disclosure can reinforce the adhesive force of the body attachable unit (20) using the over patch (5610) without increasing the size of the adhesive tape (560) and the applicator (10).

FIG. 6 is a figure for schematically illustrating a configuration of an auxiliary adhesive patch according to an embodiment of the present disclosure, and FIG. 7 is a use status figure for schematically illustrating a use state of an auxiliary adhesive patch illustrated in FIG. 6.

According to an embodiment of the present disclosure, the release paper (5620) is attached to the adhesive side of the over patch (5610), and the release paper (5620) is cut in multiple pieces formed to be separable so that each can be independently separable and removable from the over patch (5610).

At that time, at least one of pieces of the release paper (5620) formed to be separable into multiple pieces is formed to protect both a part of the pressurizing area (5612) and a part of the adhesive area (5613) and is attached to the adhesive side of the over patch (5610).

Accordingly, in a state that at least one of pieces of the release paper (5620) formed to be separable into multiple pieces is separated and removed, both a part of the pressurizing area (5612) and a part of the adhesive area (5613) are exposed simultaneously.

For example, as illustrated in FIG. 6, the release paper (5620) is formed to be cut into three (3) pieces, a position fixing release paper (5621), a first adhesive release paper (5622) and a second adhesive release paper (5623), which are separably formed. They are separably formed in a structure of being cut along a cut line (CL) as illustrated in FIG. 6.

The position fixing release paper (5621) is formed to comprise a pressurizing area protection portion (5621*a*) protecting a whole area of the pressurizing area (5612) of the over patch (5610), and an adhesive area protection portion (5621*b*) protecting a part of the adhesive area (5613) in a shape of outwardly protruding at one side of the pressurizing area protection portion (5621*a*). The pressurizing area protection portion (5621*a*) is formed in a ring shape along the pressurizing area (5612) of the over patch (5610), and the adhesive area protection area (5621*b*) is formed such that one side and the other side are symmetric with each other with respect to the center of the pressurizing area protection portion (5621*a*).

The first adhesive release paper (5622) and the second adhesive release paper (5623) are arranged on the outer portion of the pressurizing area protection portion (5621*a*) of the position fixing release paper (5621) and are formed to protect each of the remaining parts of the adhesive area (5613) of the over patch (5610). At that time, the first adhesive release paper (5622) and the second adhesive release paper (5623) can be arranged to be spaced apart from and be symmetric with each other with respect to two adhesive area protection portions (5621*b*) formed at the position fixing release paper (5621).

Additionally, a connection portion with the pressurizing area protection portion (5621*a*) of the adhesive area protection area (5621*b*) is formed to have a curved cut line (CL1), and the first adhesive release paper (5622) and the second adhesive release paper (5623) are formed to be separatably cuttable from the adhesive area protection portion (5621*a*) along the curved cut line (CL1).

According to the configurations described above, as illustrated in FIG. 7(*a*), the position fixing release paper (5621) is separated and removed from the over patch (5610) first, and, in that state, as illustrated in FIG. 7(*b*), the over patch (5610) is attached so as to cover or surround the adhesive tape (560) of the housing (510). When the over patch (5610)

is attached as described above, the over patch (5610) is in a state that the position fixing release paper (5621) is already removed, and therefore a part of the adhesive side (a partial area corresponding to the adhesive area protection portion (5621*b*)) is adhered to the human body skin while another part of the adhesive side (a partial area corresponding to the pressurizing area protection portion (5621*a*)) surrounds a whole area of the adhesive tape (560). Accordingly, in that state, the part of the adhesive side of the over patch (5610) is adhered to the human body skin, and therefore the adhesive position is fixed.

After that, as illustrated in FIG. 7(*c*), the first adhesive release paper (5622) and the second adhesive release paper (5623) positioned at both sides are separated and removed from the over patch (5610), thereby exposing the remaining adhesive side of the over patch (5610) and attaching it to the skin so that the over patch (5610) can be completely adhered to the human body skin.

Through multiple steps for separating and removing the release paper (5620), the over patch (5610) can be positionally fixed and conveniently adhered to the human body skin in a state of covering the adhesive tape (560) of the housing (510). Additionally, the first adhesive release paper (5622) and the second adhesive release paper (5623) are separately cut from the adhesive area protection portion (5621*a*) of the position fixing release paper (5621) along the curved cut line (CL1), therefore a case in which a sharp edge portion of the first adhesive release paper (5622) and the second adhesive release paper (5623) remained at the over patch (5610) pokes the skin can be prevented by attaching the over patch (5610) in a state that the position fixing release paper (5621) is separated and removed, and accordingly the attachment operation of the over patch (5610) can be performed conveniently and easily without skin pain and inconvenience.

FIG. 8 is a figure for schematically illustrating a configuration of an auxiliary adhesive patch according to another embodiment of the present disclosure, and FIG. 9 is a use status figure for schematically illustrating a use state of an auxiliary adhesive patch illustrated in FIG. 8.

The release paper (5620) of the auxiliary adhesive patch (5601) according to another embodiment of the present disclosure can be formed to be separable into a first separation release paper (5624) and a second separation release paper (5625) along two cut lines (CL) as illustrated in FIG. 8.

The first separation release paper (5624) and the second separation release paper (5625) are formed to protect a part of the pressurizing area (5612) and a part of the adhesive area (5613) of the over patch (5610), respectively, and can be formed to be symmetrical so that a whole area of the adhesive side of the over patch (5610) is divided into two pieces along a mutual cut line (CL).

A handle portion (5626) outwardly protruding from the outer portion of the over patch (5610) can be formed at each of the first separation release paper (5624) and the second separation release paper (5625), and the handle portions (5626) can be formed to be opposed to each other at a portion adjacent to the mutual cut line (CL).

According to those structures, the over patch (5610) is arranged to cover the adhesive tape (560) of the housing (510) in a state that the release paper (5620) is attached to the over patch (5610), and in this state, as illustrated in FIG. 9(*a*), the first separation release paper (5624) is separated and removed by grabbing the handle portion (5626). Like this, if the first separation release paper (5624) is separated and removed, the over patch (5620) is attached to the skin in a state that a partial area of the adhesive tape (560) of the housing (560) is covered by the pressurizing area (5612) and the adhesive area (5613) of the over patch (5610) exposed by the separation and removal of the first separation release paper (5624). After that, if the second separation release paper (5625) is separated and removed by grabbing the handle portion (5626), the attachment of the over patch (5610) to the skin is completed in a state that the remaining part of the pressurizing area (5612) and the remaining part of the adhesive area (5613) of the over patch (5610) are exposed and covers the remaining area of the adhesive tape (560) of the housing (510).

According to those structures, the auxiliary adhesive patch (5601) can be conveniently and easily, additionally adhesively-fixed to the skin in a form of covering the adhesive tape (560) of the housing (510).

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. An auxiliary adhesive patch of a body attachable unit which is capable of adhesively fixing to skin the body attachable unit for continuous blood glucose measurement comprising a housing configured to receive a sensor unit configured to be insertable into a body for the continuous blood glucose measurement inside the housing, and an adhesive tape arranged to a bottom surface of the housing and outwardly protruding along an outer portion circumference of the housing, the auxiliary adhesive patch comprising:

an over patch, wherein an adhesive side is formed at one side of the over patch, a penetrating hole which the housing is capable of penetrating is formed at a center area of the over patch, and the adhesive side of the over patch has a pressurizing area formed along a outer circumference of the penetrating hole and configured to pressurize an area of the adhesive tape outwardly protruding from an outer portion circumference of the housing and be adhered with the adhesive tape, and an adhesive area formed along an outer portion circumference of the pressurizing area and configured to be adhered to the skin; and a release paper attached to the adhesive side of the over patch in a form of being separable and removable by a user to protect the adhesive side of the over patch, wherein the release paper is cut into multiple pieces separably formed, wherein each of the multiple pieces of the release paper is independently removable from the over patch, wherein the release paper is separably formed to be cut into a position fixing release paper, a first adhesive release paper and a second adhesive release paper, wherein the first adhesive release paper and the second adhesive release paper are spaced apart from each other and symmetric to each other with respect to the position fixing release paper, and wherein the first adhesive release paper and the second adhesive release paper are configured to be positioned along the outer circumference of the adhesive tape without overlapping with the adhesive tape.

2. The auxiliary adhesive patch of the body attachable unit according to claim 1, wherein at least one of the multiple pieces of the release paper is attached to the adhesive side of the over patch to be formed to protect both a part of the pressurizing area and a part of the adhesive area of the over patch.

3. The auxiliary adhesive patch of the body attachable unit according to claim 2, wherein
the position fixing release paper comprises a pressurizing area protection portion protecting a whole area of the pressurizing area of the over patch, and an adhesive area protection portion protecting a part of the adhesive area in a structure of outwardly protruding at one side of the pressurizing area protection portion.

4. The auxiliary adhesive patch of the body attachable unit according to claim 3, wherein the pressurizing area protection portion is formed to be in a ring structure along the pressuring area of the over patch, and the adhesive area protection portion is formed such that one side and another side of the adhesive area are symmetric to each other with respect to a center of the pressurizing area protection portion.

5. The auxiliary adhesive patch of the body attachable unit according to claim 4, wherein the first adhesive release paper and the second adhesive release paper are arranged at an outside of the pressurizing area protection portion of the position fixing release paper and are formed to protect a remaining part of the adhesive area of the over patch.

6. The auxiliary adhesive patch of the body attachable unit according to claim 5, wherein the first adhesive release paper and the second adhesive release paper are spaced apart from each other and symmetric to each other with respect to two of the adhesive area protection portion formed at the position fixing release paper.

7. The auxiliary adhesive patch of the body attachable unit according to claim 6, wherein a connection portion of the adhesive area protection area with the pressurizing area protection portion is formed to have a curved cut line, and the first adhesive release paper and the second adhesive release paper are formed to be separably cuttable from the adhesive area protection portion along the curved cut line.

* * * * *